US010322162B2

(12) United States Patent
Germain et al.

(10) Patent No.: US 10,322,162 B2
(45) Date of Patent: Jun. 18, 2019

(54) METHODS AND PHARMACEUTICAL COMPOSITIONS FOR THE TREATMENT OF ISCHEMIC CONDITIONS

(71) Applicants: INSERM (INSTITUT NATIONAL DE LA SANTÉ ET DE LA RECHERCHE MÉDICALE), Paris (FR); COLLEGE DE FRANCE, Paris (FR); CENTRE NATIONAL DE LA RECHERCHE SCIENTIFIQUE (CNRS), Paris (FR); UNIVERSITÉ PARIS-EST CRÉTEIL VAL DE MARNE, Creteil (FR); ASSISTANCE PUBLIQUE-HÔPITAUX DE PARIS (APHP), Paris (FR); ECOLE NATIONALE VÉTÉRINAIRE D'ALFORT (ENVA), Maisons-Alfort (FR)

(72) Inventors: Stéphane Germain, Paris (FR); Alain Berdeaux, Creteil (FR); Renaud Tissier, Creteil (FR); Bijan Ghaleh-Marzban, Creteil (FR); Catherine Monnot, Paris (FR); Ariane Galaup, Paris (FR)

(73) Assignees: INSERM (INSTITUT NATIONAL DE LA SANTE ET DE LA RECHERCHE MEDICALE), Paris (FR); COLLEGE DE FRANCE, Paris (FR); CENTRE NATIONAL DE LA RECHERCHE SCIENTIFIQUE (CNRS), Creteil (FR); UNIVERSITE PARIS-EST CRETEIL VAL DE MARNE, Creteil (FR); ASSISTANCE PUBLIQUE-HOPITAUX DE PARIS (APHP), Paris (FR); ECOLE NATIONALE VETERINAIRE D'ALFORT (ENVA), Maisons-Alfort (FR)

( * ) Notice: Subject to any disclaimer, the term of this patent is extended or adjusted under 35 U.S.C. 154(b) by 11 days.

(21) Appl. No.: 15/541,422

(22) PCT Filed: Jan. 6, 2016

(86) PCT No.: PCT/EP2016/050108
§ 371 (c)(1),
(2) Date: Jul. 3, 2017

(87) PCT Pub. No.: WO2016/110498
PCT Pub. Date: Jul. 14, 2016

(65) Prior Publication Data
US 2018/0000892 A1    Jan. 4, 2018

(30) Foreign Application Priority Data
Jan. 6, 2015   (EP) .................... 15305008

(51) Int. Cl.
A61K 38/16    (2006.01)
A61K 38/18    (2006.01)
C07K 14/00    (2006.01)
C07K 14/575   (2006.01)
A61K 38/49    (2006.01)
A61K 45/06    (2006.01)
C07K 14/315   (2006.01)

(52) U.S. Cl.
CPC ........ *A61K 38/166* (2013.01); *A61K 38/1891* (2013.01); *A61K 38/49* (2013.01); *A61K 45/06* (2013.01); *C07K 14/315* (2013.01); *A61K 2300/00* (2013.01); *C07K 2319/30* (2013.01)

(58) Field of Classification Search
None
See application file for complete search history.

(56) References Cited

FOREIGN PATENT DOCUMENTS

WO    2011/089152 A1    7/2011

OTHER PUBLICATIONS

Wells, 1990, Biochemistry 29:8509-8517.*
Ngo et al., 1994, The Protein Folding Problem and Tertiary Structure Prediction, pp. 492-495.*
C. Bouleti et al., "Protective effects of angiopoietin-like 4 on cerebrovascular and functional damages in ischaemic stroke", European Heart Journal, Dec. 2013, pp. 3657-2668, vol. 34, No. 47.
R. Spescha et al., "Angiopoietin-like 4 and ischaemic stroke: a promising start", European Heart Journal, Dec. 2013, Dec. 2013, pp. 3603-3605, vol. 34, No. 47.
C. Bouleti et al., "Protection against mycocardial infarction and no-reflow through preservation of vascular integrity by angiopoietin-like 4", Cardiovascular Research, Mar. 15, 2012, p. P361, vol. 93, No. Suppl, Oxford University Press, GB.

(Continued)

*Primary Examiner* — Christine J Saoud
*Assistant Examiner* — Jon M Lockard
(74) *Attorney, Agent, or Firm* — W&C IP

(57) ABSTRACT

The present invention relates to methods and pharmaceutical compositions for the treatment of ischemic conditions. In particular, the present invention relates to a method of treating an ischemic condition in a subject in need thereof comprising administering the subject with a polypeptide comprising an amino acid sequence having at least 70% of identity with the amino acid sequence ranging from the amino acid residue at position 186 to the amino acid residue at position 406 in SEQ ID NO: 1.

Figure 3A:
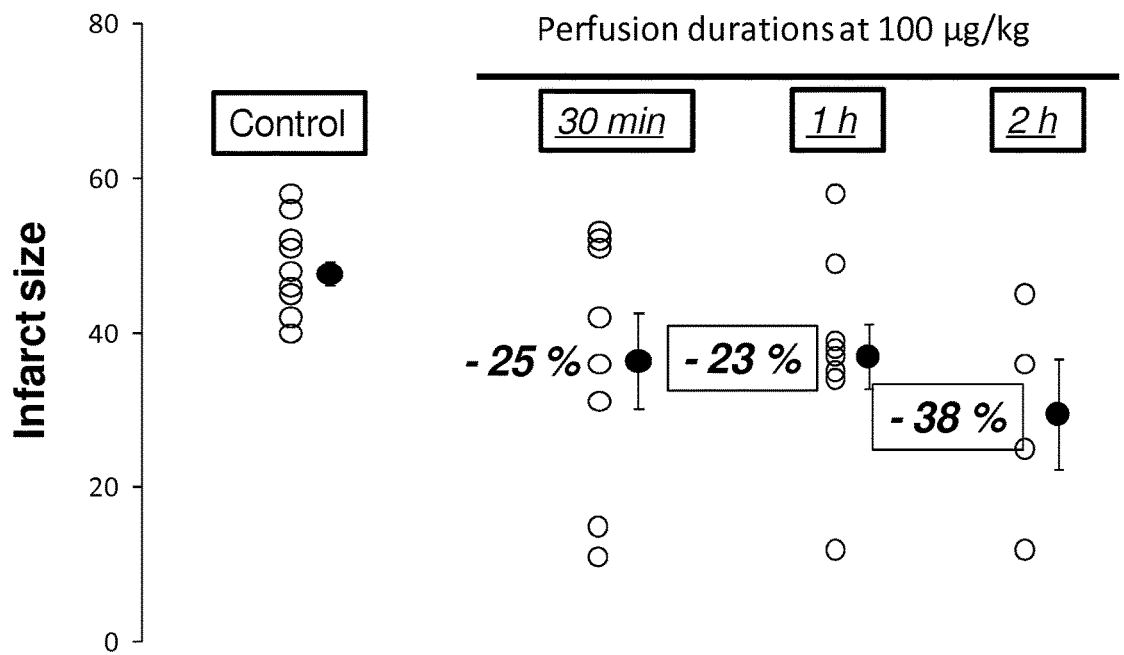

8 Claims, 3 Drawing Sheets
Specification includes a Sequence Listing.

(56) References Cited

OTHER PUBLICATIONS

C. Bouleti et al., "Protection against stroke through preservation of vascular integrity by angiopoietin-like 4 (AGPTL4)", European Heart Journal, Aug. 2012, p. 678, vol. 33, No. Suppl, Oxford University Press, GB.
"*Homo sapiens* angiopoietin-like 4 (ANGPTL4), transcript variant 1, mRNA", Database Nucleotide, Jul. 17, 2014.
"*Homo sapiens* angiopoietin-like 4 (ANGPTL4) transcript variant 3, mRNA", Database Nucleotide, Jul. 17, 2014.
"Angiopoietin-like 4 [*Homo sapiens*]", Database Protein, Jul. 15, 2006.
D. Czajkowsky et al., "Fc-fusion proteins: new developments and future perspectives", EMBO Molecular Medicine, Jul. 26, 2012, pp. 1015-1028, vol. 4, No. 10.

\* cited by examiner

SEQ ID NO:1 (GenBank: AAH23647.1)

MSGAPTAGAA LMLCAATAVL LSAQGGPVQS KSPRFASWDE
MNVLAHGLLQ LGQGLREHAE RTRSQLSALE RRLSACGSAC QGTEGSTDLP
LAPESRVDPE VLHSLQTQLK AQNSRIQQLF HKVAQQQRHL EKQHLRIQHL
QSQFGLLDHK HLDHEVAKPA RRKRLPEMAQ PVDPAHNVSR
<u>LHRLPRDCQE LFQVGERQSG LFEIQPQGSP PFLVNCKMTS
DGGWTVIQRR HDGSVDFNRP WEAYKAGFGD PHGEFWLGLE
KVHSITGDRN SRLAVQLRDW DGNAELLQFS VHLGGEDTAY
SLQLTAPVAG QLGATTVPPS GLSVPFSTWD QDHDLRRDKN
CAKSLSGGWW FGTCSHSNLN GQYFRSIPQQ RQKLKKGIFW
KTWRGRYYPL QATTMLIQPM AAEAAS</u>

Figure 1

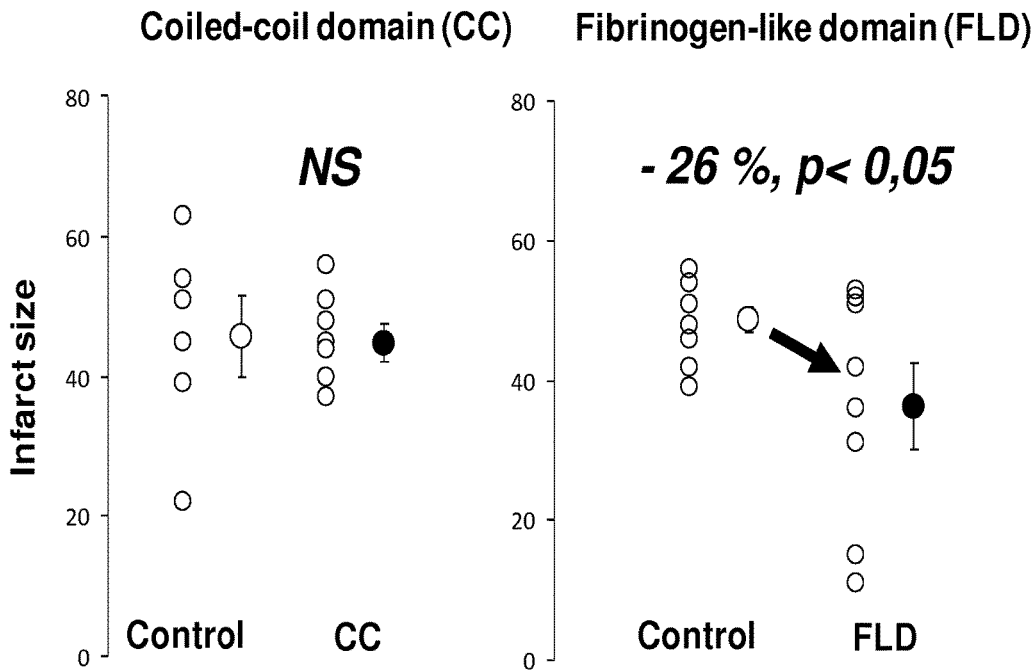

Figure 2

SEQUENCE LISTING

<160> NUMBER OF SEQ ID NOS: 1

<210> SEQ ID NO 1
<211> LENGTH: 406
<212> TYPE: PRT
<213> ORGANISM: Homo sapiens

<400> SEQUENCE: 1

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

-continued

```
Thr Cys Ser His Ser Asn Leu Asn Gly Gln Tyr Phe Arg Ser Ile Pro
        355             360             365

Gln Gln Arg Gln Lys Leu Lys Lys Gly Ile Phe Trp Lys Thr Trp Arg
    370             375             380

Gly Arg Tyr Tyr Pro Leu Gln Ala Thr Thr Met Leu Ile Gln Pro Met
385             390             395             400

Ala Ala Glu Ala Ala Ser
            405
```

METHODS AND PHARMACEUTICAL COMPOSITIONS FOR THE TREATMENT OF ISCHEMIC CONDITIONS

FIELD OF THE INVENTION

The present invention relates to methods and pharmaceutical compositions for the treatment of ischemic conditions.

BACKGROUND OF THE INVENTION

Cardiovascular disease is the leading cause of death for both men and women. More than one million people suffer from heart attacks every year in the United States alone. Cardiac ischemia, a condition characterized by reduced blood flow and oxygen to the heart muscle, or myocardium, is one hallmark of cardiovascular disease that can ultimately lead to a heart attack, or myocardial infarction. Cardiovascular disease can also result in restricted blood flow and reduced oxygen supply to other areas of the body resulting in ischemic injuries to various organs and tissues, including the brain, which can lead to stroke. Re-establishment of blood flow, or reperfusion, and re-oxygenation of the affected area following an ischemic episode is critical to limit irreversible damage. However, reperfusion also associates potentially damaging consequences. For instance, increased vascular permeability is an important contributor to edema and myocardial damage following ischemic events. Development of edema determines disruption of integrity which is detrimental to recovery and also permits extravasation of fibronectin and fibrinogen that form the provisional matrix network used by leukocytes for infiltrating. Vascular damage also contributes to the no-reflow phenomenon which is observed in 30% of patients with a reperfused anterior wall myocardial ischemia and is associated with a higher incidence of death. Leakiness of blood vessels in the heart therefore contributes to disease progression. The prevalence of cardiovascular disease necessitates the development of therapies and therapeutic agents that can effectively prevent, reduce, or counteract ischemia and ischemia-reperfusion injury resulting from a heart attack or stroke. Thus, there is a significant need for new and more effective therapies and therapeutic agents for the treatment of ischemia and ischemia-reperfusion injuries resulting from cardiovascular disease and other conditions. Recent studies show that ANGPTL4 could be suitable for the treatment of ischemic conditions, in particular stoke (European Heart Journal (2013) 34, 3657-3668) and myocardial infarction (Circulation. 2012; 125: 140-149). ANGPTL4 is a 55-kDa secreted protein which is processed in a 20-kDa and a 35-kDa, comprising the coiled-coil domain and the fibrinogen-like domain, respectively. The coiled-coil domain mediates its oligomerization which is necessary for its activities and was supposed to be the fragment responsible for the therapeutic effects observed with ANGPTL4 in ischemic conditions (see WO2011089152).

SUMMARY OF THE INVENTION

The present invention relates to methods and pharmaceutical compositions for the treatment of ischemic conditions. In particular, the present invention is defined by the claims.

DETAILED DESCRIPTION OF THE INVENTION

The inventors surprisingly show that the therapeutic effects observed with ANGPTL4 in ischemic conditions are not due to the coiled-coil domain as suggested in the prior at (WO2011089152) but are brought by the fibrinogen-like domain.

Accordingly, the present invention relates to a method of treating an ischemic condition in a subject in need thereof comprising administering the subject with a polypeptide comprising an amino acid sequence having at least 70% of identity with the amino acid sequence ranging from the amino acid residue at position 186 to the amino acid residue at position 406 in SEQ ID NO:1.

As used herein, the term "ischemic condition" has its general meaning in the art and refers to any condition that results from a restriction in blood supply in at least one organ or tissue. Ischemic condition typically results from the obstruction of a blood vessel. For example, ischemic conditions include but are not limited to renal ischemia, retinal ischemia, brain ischemia and myocardial ischemia. More particularly, the term includes but it is not limited to coronary artery bypass graft surgery, global cerebral ischemia due to cardiac arrest, focal cerebral infarction, cerebral hemorrhage, hemorrhage infarction, hypertensive hemorrhage, hemorrhage due to rupture of intracranial vascular abnormalities, subarachnoid hemorrhage due to rupture of intracranial arterial aneurysms, hypertensive encephalopathy, carotid stenosis or occlusion leading to cerebral ischemia, cardiogenic thromboembolism, stroke, spinal stroke and spinal cord injury, diseases of cerebral blood vessels: e.g., atherosclerosis, vasculitis, macular degeneration, myocardial infarction, cardiac ischemia and supraventricular tachyarrhythmia.

In the context of the invention, the term "treating" or "treatment", as used herein, means reversing and alleviating, inhibiting the progress of the ischemic condition to which such term applies condition.

In some embodiments, the method of the present invention is particularly suitable for the preservation of vascular endothelial cell barrier integrity during the treatment of ischemic conditions. As used herein, the term "vascular endothelial cell barrier" refers to the layer of cells that line the interior surface of blood vessels and act as a selective barrier between the vessel lumen and surrounding tissue, by controlling the transit of fluids, materials and cells such as myeloid cells and white blood cells into and out of the bloodstream. Excessive or prolonged increases in permeability of vascular endothelial cell barrier leads to tissue oedema/swelling. Accordingly the term "preservation of vascular endothelial cell barrier integrity" means the maintenance of the vascular endothelial cell barrier by avoiding or limiting permeability of said barrier.

In some embodiments, the method of the present invention is particularly suitable for the cardioprotection after acute myocardial infarction by preservation of vascular integrity so as to reduce infarct size, hemorrhage and no-reflow. In particular, the method of the present invention is particularly suitable for the prevention of no-reflow in the treatment of coronary heart disease, especially myocardial infarction. The term "no-reflow" has been increasingly used in published medical reports to describe microvascular obstruction and reduced myocardial flow after opening an occluded artery. In its broadest meaning, the term "preventing no-reflow" or "prevention of no-reflow" refers to reducing or avoiding the no-reflow.

In some embodiments, the method of the present invention is performed sequentially or concomitantly with a standard method for treating ischemic conditions. Typically, standard methods include reperfusion of the ischemic organ (e.g. heart) by angioplasty (e.g.; coronary, renal or carotid angioplasty), thrombolysis or coronary surgery. The term "percutaneous coronary intervention (PCI)" means coronary angioplasty which is a therapeutic procedure to treat the stenotic (narrowed) coronary arteries of the heart found in coronary heart disease. The term "thrombolysis" means the administration of thrombolytic agents. Currently available thrombolyic agents include reteplase (r-PA or Retavase), alteplase (t-PA or Activase), urokinase (Abbokinase), prourokinase, anisoylated purified streptokinase activator complex (APSAC), and streptokinase.

In some aspects, the present invention relates to a method of treating acute myocardial infarction in a patient in need thereof comprising the steps consisting of i) restoring blood supply in the cardiac ischemic tissue, and preserving the vascular endothelial cell barrier integrity of said cardiac ischemic tissue by administering to said patient a therapeutically effective amount of an ANGPTL4 polypeptide to reduce infarct size, hemorrhage, and no-reflow, where steps i) and ii) are performed sequentially or concomitantly and wherein the ANGPTL4 polypeptide comprises an amino acid sequence having at least 70% of identity with the amino acid sequence ranging from the amino acid residue at position 186 to the amino acid residue at position 406 in SEQ ID NO:1.

As used herein, the term "ANGPTL4" has its general meaning in the art and refers to the Angiopoietin-like protein 4. An exemplary human amino sequence for ANGPTL4 is SEQ ID NO:1. ANGPTL4 is a 55-kDa secreted protein which is processed in a 20-kDa fragment and a 35-kDa fragment, comprising the coiled-coil domain and the fibrinogen-like domain, respectively. The coiled-coil domain consists of the amino acid sequence which ranges from the amino acid residue at position 22 to the amino acid residue at position 170. The fibrinogen-like domain consists of the amino acid sequence which ranges from the amino acid residue at position 186 to the amino acid residue at position 406 (see FIG. 1).

According to the invention to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99, or 100% of identity with the second amino acid sequence. Amino acid sequence identity is typically determined using a suitable sequence alignment algorithm and default parameters, such as BLAST P (Karlin and Altschul, 30 1990). In particular the polypeptide of the invention is a functional conservative variant of the polypeptide having an amino acid sequence ranging from the amino acid residue at position 186 to the amino acid residue at position 406 in SEQ ID NO: 1. As used herein the term "function-conservative variant" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Accordingly, a function-conservative variant" also includes a polypeptide which has at least 70% amino acid identity and which has the same or substantially similar properties or functions as the native polypeptide to which it is compared. Functional properties of the polypeptide of the invention could typically be assessed in any functional assay as described in the EXAMPLE. In some embodiments, the polypeptide of the present invention comprises an amino acid sequence having at least 80% of identity with the amino acid sequence ranging from the amino acid residue at position 186 to the amino acid residue at position 406 in SEQ ID NO:1. In some embodiments, the polypeptide of the present invention comprises an amino acid sequence having at least 90% of identity with the amino acid sequence ranging from the amino acid residue at position 186 to the amino acid residue at position 406 in SEQ ID NO:1. In some embodiments, the polypeptide of the present invention comprises an amino acid sequence having at least 95% of identity with the amino acid sequence ranging from the amino acid residue at position 186 to the amino acid residue at position 406 in SEQ ID NO:1.

In some embodiments, the amino acid sequence of the polypeptide of the invention does not consist of SEQ ID NO:1.

In some embodiments the polypeptide of the present invention comprises an amino acid sequence having at least 70% of identity with the amino acid sequence ranging from the amino acid residue at position 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; or 185 to the amino acid residue at position 406 in SEQ ID NO:1.

In some embodiments, it is contemplated that the polypeptides of the invention are modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

In some embodiments, the polypeptide of the invention is fused a Fc domain of an immunoglobulin. Suitable immunoglobins are IgG, IgM, IgA, IgD, and IgE. IgG and IgA are preferred IgGs are most preferred, e.g. an IgG1. Said Fc domain may be a complete Fc domain or a function-conservative variant thereof. The polypeptide of the invention may be linked to the Fc domain by a linker. The linker may consist of about 1 to 100, preferably 1 to 10 amino acid residues.

According to the invention, the polypeptide of the invention may be produced by conventional automated peptide synthesis methods or by recombinant expression. General principles for designing and making proteins are well known to those of skill in the art. The polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides. A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein. In the recombinant production of the polypeptides of the invention, it would be necessary to employ vectors comprising polynucleotide molecules for encoding the polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation. The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed. The choice of a suitable expression vector for expression of the peptides or polypeptides of the invention will of course depend upon the specific host cell to be used, and is within the skill of the ordinary artisan. Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the polypeptide of interest. Thus, a promoter nucleotide sequence is operably linked to a given DNA sequence if the promoter nucleotide sequence directs the transcription of the sequence.

In some aspects, the present invention relates to a method of treating an ischemic condition in a subject in need thereof comprising administering the subject with nucleic acid molecule encoding for a polypeptide of the present invention. Typically, said nucleic acid molecule is a DNA or RNA molecule, which may be included in any suitable vector, such as a plasmid, cosmid, episome, artificial chromosome, phage or a viral vector as above described.

By a "therapeutically effective amount" is meant a sufficient amount of the polypeptide to treat the ischemic condition at a reasonable benefit/risk ratio applicable to any medical treatment. It will be understood that the total usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

Typically the active ingredient of the present invention (i.e. the polypeptide or the nucleic acid encoding thereof) is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The invention will be further illustrated by the following figures and examples. However, these examples and figures should not be interpreted in any way as limiting the scope of the present invention.

FIGURES

FIG. 1 shows the amino acid sequence of ANGPTL4, the fibrinogen-like domain; (FLD) corresponds to the sequence in bold and underlined in the whole sequence of ANGPTL4.

Figure 3B:
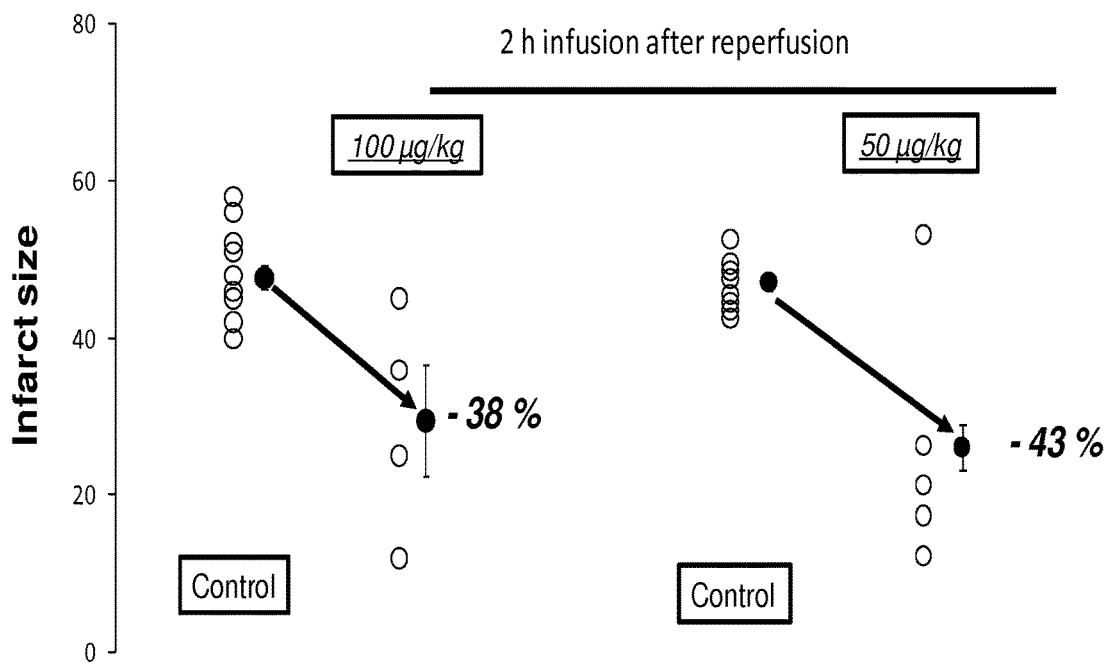

FIG. 2 shows the comparison between the coiled-coil domain (CCD) polypeptide and the fibrinogen-like domain (FLD) polypeptide in the reduction of infarct size FIG. 3 shows that the ANGPTL4 FLD polypeptide administration protocol (bolus+perfusion) leads to a significant reduction of the infarct size in mice that received the polypeptide compared to controls A. ANGPTL4 FLD polypeptide (bolus+various duration of infusion after reperfusion) in mice. B. ANGPTL4 polypeptide (bolus+2 h infusion after reperfusion with 2 doses) in mice.

Figure 4:
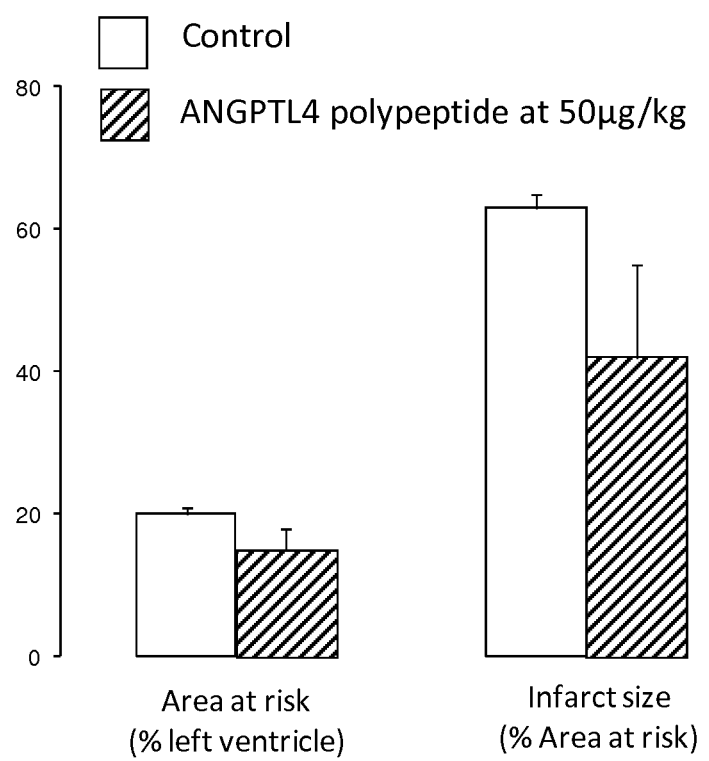

FIG. 4 shows that administration of ANGPTL4 FLD polypeptide (bolus+perfusion) leads to a significant reduction of the infarct size in pigs.

EXAMPLE 1: COMPARISON BETWEEN THE CCD POLYPEPTIDE AND THE FLD POLYPEPTIDE OF ANGPTL4

Mice were anesthetized by an intraperitoneal injection of sodium pentobarbital. Coronary artery occlusion (CAO) was induced during 30-min. One min before reperfusion, the animals received a bolus of the human recombinant CC (coiled-coil) or FLD (fibrinogen-like domain) polypeptide of ANGPTL4 (or vehicle for the control animals). Just after reperfusion (i.e. release of the occlusion) the animals were infused with an amount of the same recombinant polypeptide (or vehicle for the control animals) for 30 min. The infarct area was then identified by Evans blue staining at 24 h after ischemia when the animals were euthanized. The results are depicted in FIG. 2 and clearly show that the coiled-coil domain (CC) does not confer protection in contrast to the fibrinogen-like domain (FLD) domain. In conclusion, the therapeutic effects observed with ANGPTL4 in ischemic conditions are not due to the coiled-coil domain as suggested in the prior at (WO2011089152) but are brought by the fibrinogen-like domain.

EXAMPLE 2: MOUSE MODEL OF MYOCARDIAL INFARCTION

Mice were anesthetized by an intraperitoneal injection of sodium pentobarbital. Coronary artery occlusion (CAO) was induced during 30-min. One min before reperfusion, the animals received a bolus of the human recombinant FLD (fibrinogen-like domain) polypeptide of ANGPTL4 (or vehicle for the control animals). Just after reperfusion (i.e. release of the occlusion) the animals were infused with an amount of the same recombinant FLD polypeptide (or vehicle for the control animals) for 30 min, 1 hour and 2 hours. The infarct area was then identified by Evans blue staining at 24 h after ischemia when the animals were euthanized. The results are depicted in FIG. 3 and clearly show that this protocol of administration lead to a significant reduction of the infarct size in the animals which received the polypeptide.

EXAMPLE 3: PIG MODEL OF MYOCARDIAL INFARCTION

Coronary artery occlusion (CAO) was induced during 30-min. One min before reperfusion, the animals received a bolus of human recombinant FLD (fibrinogen-like domain) polypeptide of ANGPTL4 (or vehicle for the control animals). Just after reperfusion (i.e. release of the occlusion) the animals were infused with an amount of the same FLD polypeptide (or vehicle for the control animals) for 2 hours. The infarct area was then identified by Evans blue staining at 24 h after ischemia when the animals were euthanized. The results are depicted in FIG. 4 and clearly show that this protocol of administration lead to a significant reduction of the infarct size in the animals which received the polypeptide.

REFERENCES

Throughout this application, various references describe the state of the art to which this invention pertains. The disclosures of these references are hereby incorporated by reference into the present disclosure.

The invention claimed is:

1. A method of treating an ischemic organ or tissue in a subject in need thereof comprising administering to the subject a synthetic ANGPTL4 polypeptide fragment comprising an amino acid sequence as set forth from position 186 to position 406 in SEQ ID NO:1, provided that said polypeptide is not SEQ ID NO:1, wherein the synthetic ANGPTL4 polypeptide fragment is administered in an amount sufficient to preserve vascular endothelial cell barrier integrity in the ischemic organ or tissue.

2. The method of claim 1 wherein the ischemic organ or tissue is the result of renal ischemia, retinal ischemia, brain ischemia or myocardial ischemia.

3. The method of claim 1 wherein the subject is suffering from at least one condition is-selected from the group consisting of coronary artery bypass graft surgery, global cerebral ischemia due to cardiac arrest, focal cerebral infarction, cerebral hemorrhage, hemorrhage infarction, hypertensive hemorrhage, hemorrhage due to rupture of intracranial vascular abnormalities, subarachnoid hemorrhage due to rupture of intracranial arterial aneurysms, hypertensive encephalopathy, carotid stenosis or occlusion leading to cerebral ischemia, cardiogenic thromboembolism, stroke, spinal stroke and spinal cord injury, vasculitis, macular degeneration, myocardial infarction, cardiac ischemia and supraventricular tachyarrhythmia.

4. The method of claim 1 wherein the synthetic ANGPTL4 polypeptide fragment is administered sequentially or concomitantly with a standard method selected from the group consisting of reperfusion of the ischemic organ by angioplasty, percutaneous coronary intervention, thrombolysis and coronary surgery.

5. The method of claim 1 wherein the synthetic ANGPTL4 polypeptide fragment is administered sequentially or concomitantly with a thrombolyic agent selected from the group consisting of reteplase, alteplase, urokinase, prourokinase, anisoylated purified streptokinase activator complex, and streptokinase.

6. The method of claim 1 wherein the synthetic ANGPTL4 polypeptide fragment is fused to a Fc domain of an immunoglobulin.

7. A method of treating acute myocardial infarction in a patient in need thereof comprising the steps of i) restoring blood supply in cardiac ischemic tissue, and ii) preserving vascular endothelial cell bather integrity of said cardiac ischemic tissue by administering to said patient a therapeutically effective amount of a synthetic ANGPTL4 polypeptide fragment to reduce infarct size, hemorrhage, and no-reflow, where steps i) and ii) are performed sequentially or concomitantly and wherein the synthetic ANGPTL4 polypeptide fragment comprises an amino acid sequence as set forth from position 186 to position 406 in SEQ ID NO:1, provided that said polypeptide is not SEQ ID NO:1.

8. A method of treating at least one ischemic organ or tissue in a patient in need thereof, comprising the steps of
restoring blood supply in the at least one ischemic organ or tissue selected from the group consisting of heart, kidney, retina and brain; and
administering to said patient a therapeutically effective amount of a synthetic ANGPTL4 polypeptide fragment having an amino acid sequence as set forth in SEQ ID NO:1 from position 186 to position 406, provided that said polypeptide is not SEQ ID NO:1;
wherein said restoring and administering steps are performed sequentially or concomitantly, and
wherein vascular endothelial cell barrier integrity of the at least one ischemic organ or tissue is preserved.

* * * * *